(12) United States Patent
Koslow (10) Patent No.: US 6,630,016 B2
(45) Date of Patent: Oct. 7, 2003

(54) MICROPOROUS FILTER MEDIA, FILTRATION SYSTEMS CONTAINING SAME, AND METHODS OF MAKING AND USING

(75) Inventor: Evan E. Koslow, Weston, CT (US)

(73) Assignee: Koslow Technologies Corp., Orange, CT (US)

( * ) Notice: Subject to any disclaimer, the term of this patent is extended or adjusted under 35 U.S.C. 154(b) by 0 days.

(21) Appl. No.: 10/290,803

(22) Filed: Nov. 8, 2002

(65) Prior Publication Data

US 2003/0140785 A1 Jul. 31, 2003

Related U.S. Application Data (60) Provisional application No. 60/354,062, filed on Jan. 31, 2002.

(51) Int. Cl.[7] .................................................. C02F 1/50
(52) U.S. Cl. ............................. 95/285; 96/226; 96/153; 55/524; 55/DIG. 5; 210/764; 210/501; 210/502.1; 210/506; 264/122; 264/DIG. 48; 156/283; 427/245
(58) Field of Search ......................... 95/273, 274, 285; 96/223, 226, 227, 153; 55/524, DIG. 5; 210/764, 501, 502.1, 504, 506; 422/1, 120; 264/122, DIG. 48; 156/283; 427/243, 245

(56) References Cited

U.S. PATENT DOCUMENTS

| | | | | |
|---|---|---|---|---|
| 2,261,002 A | * | 10/1941 | Ritter | 528/397 |
| 2,271,378 A | * | 1/1942 | Searle | 424/78.08 |
| 2,388,614 A | * | 11/1945 | Kirby et al. | 514/556 |
| 2,454,547 A | * | 11/1948 | Bock et al. | 564/292 |
| 4,682,992 A | * | 7/1987 | Fuchs | 96/226 |
| 4,828,698 A | * | 5/1989 | Jewell et al. | 210/266 |
| 5,006,267 A | * | 4/1991 | Vaughn et al. | 210/755 |
| 5,019,311 A | * | 5/1991 | Koslow | 264/122 |
| 5,792,513 A | * | 8/1998 | Koslow et al. | 427/195 |
| 5,876,489 A | * | 3/1999 | Kunisaki et al. | 96/226 |
| 6,190,437 B1 | * | 2/2001 | Forsyth | 95/90 |
| 6,471,876 B1 | * | 10/2002 | Hansen et al. | 210/764 |

FOREIGN PATENT DOCUMENTS

| WO | WO 97/23594 | * | 7/1997 |
|---|---|---|---|
| WO | WO 01/07090 | * | 2/2003 |

OTHER PUBLICATIONS

Koslow, E.E., *Microbiological Interception Using Modified Carbon Blocks*, Sep. 26, 2002, International Activated Carbon Conference.

Koslow, E.E., *The Quest for the Holy Grail, Microbiological Carbon Block Filters*, Water Conditioning & Purification, Aug. 2002.

* cited by examiner

*Primary Examiner*—Frank M. Lawrence
(74) *Attorney, Agent, or Firm*—Shirley S. Ma (57) ABSTRACT

The invention is directed to a microbiological interception enhanced filter medium comprising a microporous structure having a mean flow path of less than about 2 microns and made of an array of active particles. At least a portion of the surface of microporous structure has formed thereon a microbiological interception enhancing agent comprising a cationic material in combination with a biologically active metal. A microbiological interception enhanced filter medium of the present invention provides greater than about 4 log viral interception, and greater than about 6 log bacterial interception.

38 Claims, 1 Drawing Sheet

FIG. 1

MICROPOROUS FILTER MEDIA, FILTRATION SYSTEMS CONTAINING SAME, AND METHODS OF MAKING AND USING

This application claims priority from U.S. Provisional Application Ser. No. 60/354,062 filed on Jan. 31, 2002.

The present invention is directed to filter media having microbiological interception capability, filtration systems containing such filter media, and methods of making and using same.

Modern consumer water filters often provide "health claims" including reduction of particulates, heavy metals, toxic organic chemicals, and select microbiological threats. These filtration systems have been able to intercept microorganisms such as Cryptosporidium and Giardia using roughly 1.0 micron structures. However, in order to provide microbiological interception of even smaller microbiological threats such as viruses, a filter medium having a submicron microporous structure is required. Prior art filtration systems often attempt to achieve broad microbiological interception using filter media with insufficiently small pore size and with poor physical integrity. The balance between the necessary pore structure required for successful microbiological interception and satisfactory filter performance has not been achieved.

SUMMARY OF THE INVENTION

The present invention is directed to, in a first aspect, a filter medium comprising: a microporous structure comprising an array of active particles, the microporous structure having a mean flow path of less than about 2 microns; and a microbiological interception enhancing agent comprising a cationic material having a medium to high charge density and a molecular weight greater than about 5000 Daltons, adsorbed on at least a portion of the microporous structure, and a biologically active metal in direct proximity to the cationic material and also on at least a portion of the microporous structure.

In another aspect, the present invention is directed to a filter system comprising: a housing having an inlet and an outlet; a filter medium situated within the housing in fluid communication with the inlet and outlet, the filter medium comprising: a microporous structure having a mean flow path of less than about 2 microns comprising active particles of activated carbon, activated alumina, zeolites, diatomaceous earth, silicates, aluminosilicates, titanates, bone char, calcium hydroxyapatite, manganese oxides, iron oxides, magnesia, perlite, talc, polymeric particulates, clay, iodated resins, ion exchange resins, ceramics, or combinations thereof; and a microbiological interception enhancing agent comprising a cationic material having a high charge density, a molecular weight greater than about 5000 Daltons and having an associated counter ion therewith, the cationic material adsorbed on at least a portion of the microporous structure, and wherein a biologically active metal is caused to precipitate with at least a portion of the counter ion associated with the cationic material, wherein a microbiologically contaminated influent flowing through the housing and contacting the filter medium has at least about 4 log reduction in microbiological contaminants in an effluent flowing from the housing.

In yet another aspect, the present invention is directed to a process of making a filter medium having enhanced microbiological interception capability comprising the steps of: providing active particles having an average particle size of about 0.1 microns to about 5,000 microns; treating the active particles with a microbiological interception enhancing agent comprising a cationic material having a high charge density and a molecular weight greater than about 5000 Daltons in combination with a biologically active metal; and forming the treated active particles into a microporous structure having a mean flow path of less than about 2 microns.

In still yet another aspect, the present invention is directed to a process of making a filter medium having enhanced microbiological interception capability comprising the steps of: providing active particles having an average particle size of about 0.1 microns to about 5,000 microns; coalescing the active particles into a microporous structure having a mean flow path of less than about 2 microns; and treating the microporous structure with a microbiological interception enhancing agent comprising a cationic material having a high charge density and a molecular weight greater than about 5000 Daltons in combination with a biologically active metal.

In a further aspect, the present invention is directed to a method of removing microbiological contaminants from a fluid comprising the steps of providing a filter medium comprising a microporous structure comprising active particles and having a mean flow path of less than about 2 microns; and a microbiological interception enhancing agent comprising a cationic material having a medium to high charge density and a molecular weight greater than about 5000 Daltons in combination with a biologically active metal, adsorbed on at least a portion of the microporous structure; contacting a microbiologically contaminated fluid to the filter medium for a period of time of less than or equal to about 12 seconds; and obtaining an effluent having greater than about 4 log reduction of microbiological contaminants.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, can best be understood by reference to the description of the preferred embodiment(s) which follows, taken in conjunction with the accompanying drawings in which:

DETAILED DESCRIPTION OF THE PREFERRED EMBODIMENT(s)

Figure 1:
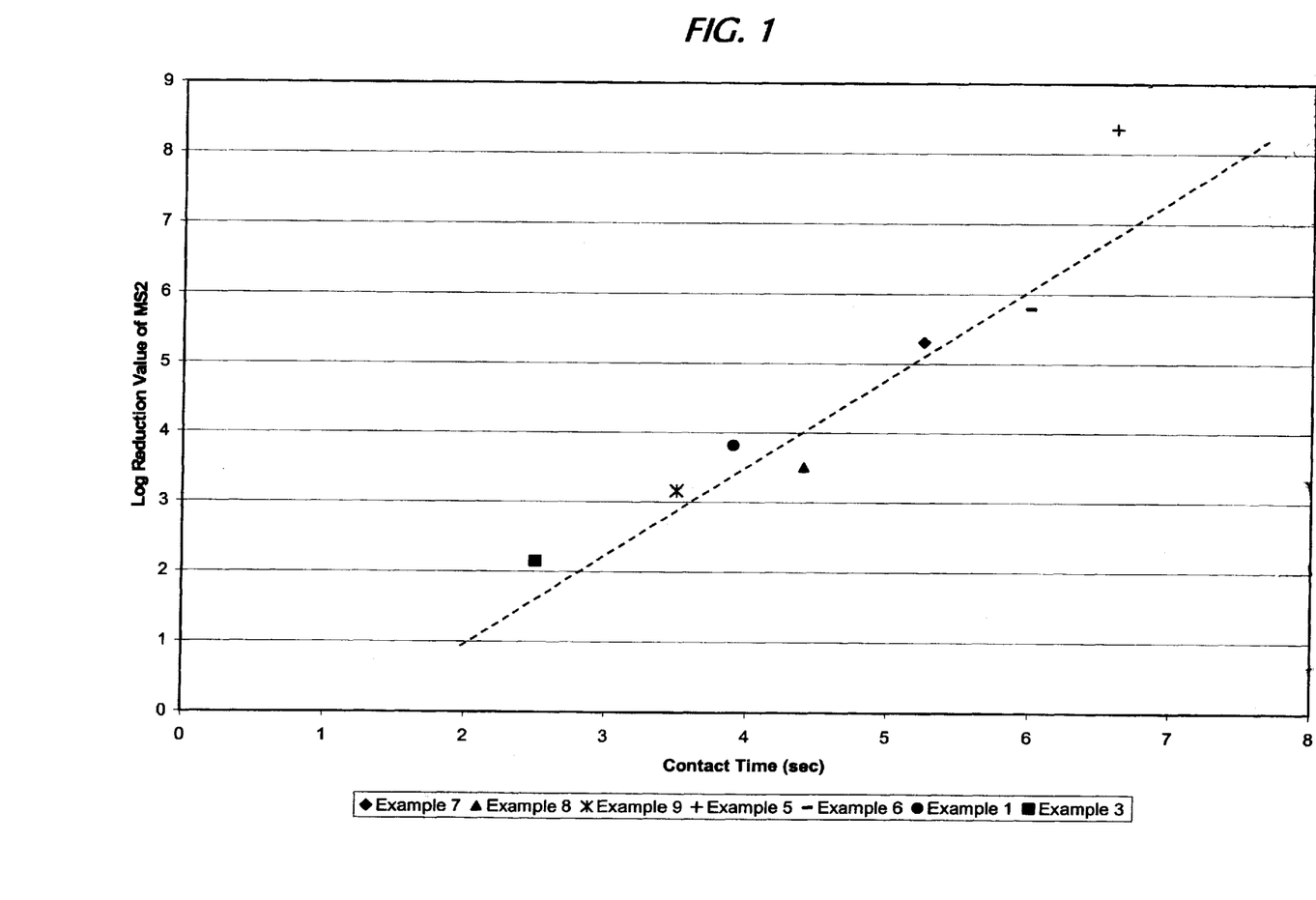
FIG. 1 is a graph plotting the empty bed contact time versus the log reduction values of MS2 bacteriophage of the microbiological interception enhanced activated carbon filter medium of the present invention.

In describing the preferred embodiment of the present invention, reference will be made herein to FIG. 1 of the drawings.

Definitions

As used herein, "absorbent" shall mean any material that is capable of drawing a substance into its inner structure.

As used herein, "adsorbent" shall mean any material that is capable of drawing a substance to its surface by physical means and without any covalent bonding.

As used herein, "binder" shall mean a material used principally to hold other materials together.

As used herein, "contaminant reduction" shall mean attenuation of an impurity in a fluid that is intercepted, removed, and/or rendered inactive, chemically, mechanically or biologically, in order to render the fluid safer as, for example, for human use, or more useful as in industrial applications.

As used herein, "empty bed contact time" or "EBCT" shall mean a measure of how much contact occurs between particles, such as, for example, activated carbon, and a fluid as the fluid flows through the bed of particles.

As used herein, "fiber" shall mean a solid that is characterized by a high aspect ratio of length to diameter of, for example, several hundred to one. Any discussion of fibers shall also be deemed to include whiskers.

As used herein, "filter medium" shall mean a material that performs fluid filtration.

As used herein, "fluid" shall mean a liquid, gas, or combination thereof.

As used herein, "intercept" or "interception" are taken to mean interfering with, or stopping the passage of, so as to affect, remove, inactivate or influence.

As used herein, "log reduction value" or "LRV" shall mean the logio of the number of organisms in the influent divided by the number of organisms in the effluent after passing through a filter.

As used herein, "metal" shall mean to include the salts, colloids, precipitates, base metal, and all other forms of a given metallic element.

As used herein, "microbiological interception enhanced filter medium" shall mean a filter medium having a microporous structure where at least a portion of the microporous structure is treated with a microbiological interception enhancing agent.

As used herein, "microbiological interception enhancing agent" shall mean a cationic material having a counter ion associated therewith in combination with a biologically active metal.

As used herein, "microorganism" shall mean any living organism that can be suspended in a fluid, including but not limited to, bacteria, viruses, fungi, protozoa, and reproductive forms thereof including cysts and spores.

As used herein, "microporous structure" shall mean a structure that has a mean flow path less than about 2.0 microns, and often less than about 1.0 micron.

As used herein, "natural organic matter" or "NOM" shall mean organic matter often found in potable or non-potable water, a portion of which reduces or inhibits the streaming, or zeta, potential of a positively charged filter medium. Exemplary of NOM are polyanionic acids such as, but not limited to, humic acid and fulvic acid.

As used herein, "nonwoven" means a web or fabric or other medium having a structure of individual fibers that are interlaid, but not in a highly organized manner as in a knitted or woven fabric. Nonwoven webs generally can be prepared by methods that are well known in the art. Examples of such processes include, but are not limited to, and by way of illustration only, meltblowing, spunbonding, carding, and air laying.

As used herein, "particle" shall mean a solid having a size range from colloidal to macroscopic, and with no specific limitation on shape, but generally of a limited length to width ratio.

As used herein, "prefilter" shall mean a filter medium generally located upstream from other filtration layers, structures or devices and capable of reducing particulate contaminants prior to the influent contacting subsequent filtration layers, structures or devices.

As used herein, "whisker" shall mean a filament having a limited aspect ratio and intermediate between the aspect ratio of a particle and a fiber. Any discussion of fibers shall also be deemed to include whiskers.

The Microbiological Interception Enhanced Filter Medium

A filter medium of the present invention has a microporous structure that provides microbiological interception capability using a combination of an appropriate pore structure and a chemical treatment. The microporous structure comprises an array of active particles that have a specific pore structure, as well as adsorbent and/or absorbent properties. The array can be a solid composite block, a monolith, a ceramic candle, a flat-sheet composite of bonded or immobilized particles formed into a coherent medium using a binder or supporting fibers, and the like. These particle arrays can be made through processes known in the art such as, for example, extrusion, molding, or slip casting. The chemical treatment process used to treat the surface of the microporous structure utilizes a synergistic interaction between a cationic material and a biologically active metal, that when combined, provide broad-spectrum reduction of microbiological contaminants on contact. The charge provided by the cationic material to the filter medium aids in electro-kinetic interception of microbiological contaminants, while the tight pore structure provides a short diffusion path and, therefore, rapid diffusion kinetics of microbiological contaminants in a flowing fluid to a surface of the microporous structure. The microporous structure also provides supplemental direct mechanical interception of microbiological contaminants. Due to the dominant role of diffusion for the interception of extremely small particles, there is a direct correlation between the log reduction value of viral particles and the contact time of the influent within the filter medium, rather than a dependence upon the thickness of the filter medium.

Characteristics of the Microbiological Interception Enhanced Filter Medium

In order to provide full microbiological interception capability, the microbiological interception enhanced filter medium of the present invention has a mean flow path of less than about 2 microns, and more preferably less than or equal to about 1 micron. If the mean flow path is greater than about 2 microns, then the diffusion efficiency of viral particles rapidly declines and efficient biological interception fails. The volume of the microbiological interception enhanced filter medium of the present invention compared to the flow rate of fluid through the filter medium must be sufficient to provide a contact time adequate for the contaminants to diffuse to a surface of the filter medium. To provide enhanced electro-kinetic interception of microorganisms, of which the majority are negatively charged, at least a portion of the microporous structure is coated with a cationic material to produce a positive charge on at least a portion of such microporous structure. The cationic material is of sufficient molecular size to prevent fouling of the micropores and mezo-pores of the active particles.

Natural organic matter (NOM), such as polyanionic acids, i.e., humic acid or fulvic acid, that can reduce or remove the charge on the microbiological interception enhanced filter medium, is preferably prevented from contacting the charged microporous structure through the use of an adsorbent prefilter that substantially removes the NOM. It is possible to incorporate the NOM removing material directly into the microbiological interception enhanced filter medium, thereby eliminating the need for a separate adsorbent prefilter. Also, depending on the type of active particles used, the upstream portion of the microbiological interception enhanced filter medium itself can naturally reduce or remove NOM as well and prevent a loss of performance of the downstream portions of the microbiological interception enhanced filter medium.

When used in the context of a gravity-flow water filtration system, it is preferable that the microbiological interception enhanced filter medium be made with hydrophilic materials or treated with a wetting agent to provide good, spontaneous wettability. Alternatively, in other applications, the microbiological interception enhanced filter medium can be treated to provide either a hydrophilic or hydrophobic characteristic as needed. It is possible that the microbiological interception enhanced filter medium can have both positively and negatively charged and uncharged regions, and/or hydrophilic and hydrophobic regions. For example, the negatively charged regions can be used to enhance the interception of less common positively charged contaminants and uncharged hydrophobic regions can be used to provide enhanced interception of contaminants that are attracted to hydrophobic surfaces.

The Active Particles

The microbiological interception enhanced filter medium having enhanced microbiological interception capabilities of the present invention comprises an array of adsorbent and/or absorbent active particles having a particle size distribution of 80×325 mesh with about 20% to about 24% pan (particles smaller than −325 mesh). The active particles can include, but are not limited to, activated carbon, activated alumina, zeolites, diatomaceous earth, silicates, aluminosilicates, titanates, bone char, calcium hydroxyapatite, manganese oxides, iron oxides, magnesia, perlite, talc, polymeric particulates, clay, iodated resins, ion exchange resins, ceramics, super absorbent polymers (SAPs), and combinations thereof. A microbiological interception enhanced filter medium having requisite properties can be obtained by combining one or more of these active particles.

One preferred microporous structure comprises active particles of activated carbon that naturally resist fouling by NOM and is efficient at adsorbing the potentially interfering NOM in peripheral regions of the microporous structure while protecting inner regions. Preferably, the activated carbon is acid washed bituminous coal-based activated carbon. Commercially available activated carbon suitable for use in the present invention can be obtained from Calgon Carbon Corporation of Pittsburgh, Penn., under the trade designation TOG-NDS or from California Carbon Company of Wilmington, Calif., under the trade designation 1240ALC. Most preferably, the active particles are comprised of acid washed bituminous coal-based activated carbon from Calgon Carbon Corporation, having a particle size distribution as follows: about 3% to about 7%, preferably about 5%, 80 mesh size particles; about 12% to about 18%, preferably about 15% 100 mesh; about 44% to about 50%, preferably 47% 200 mesh; about 8% to about 14%, preferably about 11% 325 mesh; and about 20% to about 24% pan, preferably about 22% pan.

The Microbiological Interception Enhancing Agent

The active particles of the microporous structure are chemically treated with a microbiological interception enhancing agent capable of creating a positive charge on the surface of the active particles. The chemical treatment produces a strong positive charge upon the treated surfaces as measured using streaming potential analysis and this positive charge is retained at pH values below 10. A cationic metal complex is formed on at least a portion of the surface of the active particles by treating the active particles with a cationic material. The cationic material may be a small charged molecule or a linear or branched polymer having positively charged atoms along the length of the polymer chain.

If the cationic material is a polymer, the charge density is preferably greater than about 1 charged atom per about every 20 Angstroms, preferably greater than about 1 charged atom per about every 10 Angstroms, and more preferably greater than about 1 charged atom per about every 5 Angstroms of molecular length. The higher the charge density on the cationic material, the higher the concentration of the counter ion associated therewith. A high concentration of an appropriate counter ion can be used to drive the precipitation of a metal complex. The high charge density of the cationic polymer provides the ability to adsorb and significantly reverse the normal negative charge of active particles such as carbon. The cationic material should consistently provide a highly positively charged surface to the microporous structure as determined by a streaming or zeta potential analyzer, whether in a high or low pH environment.

The use of a polymer of sufficiently high molecular weight allows treatment of the surfaces of the active particles without serious attendant impact upon the adsorptive capabilities of the mezo-pores and micro-pores of the active particles. The cationic material can have a molecular weight greater than or equal to about 5000 Daltons, preferably greater than or equal to 100,000 Dalton, more preferably greater than or equal to about 400,000 Daltons, and can be greater than or equal to about 5,000,000 Daltons.

The cationic material includes, but is not limited to, quaternized amines, quaternized amides, quaternary ammonium salts, quaternized imides, benzalkonium compounds, biguanides, cationic aminosilicon compounds, cationic cellulose derivatives, cationic starches, quaternized polyglycol amine condensates, quaternized collagen polypeptides, cationic chitin derivatives, cationic guar gum, colloids such as cationic melamine-formaldehyde acid colloids, inorganic treated silica colloids, polyamide-epichlorohydrin resin, cationic acrylamides, polymers and copolymers thereof, combinations thereof, and the like. Charged molecules useful for this application can be small molecules with a single charged unit and capable of being attached to at least a portion of the microporous structure. The cationic material preferably has one or more counter ions associated therewith which, when exposed to a biologically active metal salt solution, cause preferential precipitation of the metal in proximity to the cationic surface to form a cationic metal precipitate complex.

Exemplary of amines may be pyrroles, epichlorohydrin derived amines, polymers thereof, and the like. Exemplary of amides may be those polyamides disclosed in International Patent Application No. WO 01/07090, and the like. Exemplary of quaternary ammonium salts may be homopolymers of diallyl dimethyl ammonium halide, epichlorohydrin derived polyquaternary amine polymers, quaternary ammonium salts derived from diamines and dihalides such as those disclosed in U.S. Pat. Nos. 2,261,002, 2,271,378, 2,388,614, and 2,454,547, all of which are incorporated by reference, and in International Patent Application No. WO 97/23594, also incorporated by reference, polyhexamethylenedimethylammonium bromide, and the like. The cationic material may be chemically bonded, adsorbed, or crosslinked to itself and/or to the active particles.

Furthermore, other materials suitable for use as the cationic material include BIOSHIELD® available from Bio-Shield Technologies, Inc., Norcross, Ga. BIOSHIELD® is an organosilane product including approximately 5% by weight octadecylaminodimethyltrimethoxysilylpropyl ammonium chloride and less than 3% chloropropyltrimethoxysilane. Another material that may be used is SURFACINE®, available from Surfacine Development Company LLC, Tyngsboro, Mass. SURFACINE® comprises a three-dimensional polymeric network obtained by reacting poly(hexamethylenebiguanide) (PHMB) with 4,4'-methlyene-bis-N,N-dilycidylaniline (MBGDA), a crosslinking agent, to covalently bond the PHMB to a polymeric surface. Silver, in the form of silver iodide, is introduced into the network, and is trapped as submicron-sized particles. The combination is an effective biocide, which may be used in the present invention. Depending upon the active particles, the MBGDA may or may not crosslink the PHMB to the microporous structure.

The cationic material is exposed to a biologically active metal salt solution such that the metal complex precipitates onto at least a portion of the surface of at least some of the active particles. For this purpose, the metals that are biologically active are preferred. Such biologically active metals include, but are not limited to, silver, copper, zinc, cadmium, mercury, antimony, gold, aluminum, platinum, palladium, and combinations thereof. The most preferred biologically active metals are silver and copper. The biologically active metal salt solution is preferably selected such that the metal and the counter ion of the cationic material are substantially insoluble in an aqueous environment to drive precipitation of the metal complex. Preferably, the metal is present in an amount of about 0.01% to about 2.0% by weight of the total composition.

A particularly useful microbiological interception enhancing agent is a silver-amine-halide complex. The cationic amine is preferably a homopolymer of diallyl dimethyl ammonium halide having a molecular weight of about 400,000 Daltons or other quaternary ammonium salts having a similar charge density and molecular weight. A homopolymer of diallyl dimethyl ammonium chloride useful in the present invention is commercially available from Nalco Chemical Company of Naperville, Ill., under the tradename MERQUAT® 100. The chloride counter ion may be replaced with a bromide or iodide counter ion. When contacted with a silver nitrate solution, the silver-amine-halide complex precipitates on at least a portion of the active particles of the microporous structure of the microbiological interception enhanced filter medium.

Where the active particles comprise activated carbon, the cationic material preferably has a high charge density and a sufficiently high molecular weight to create a strong attraction and high coordination energy with the negatively charged surface groups of activated carbon. Also, the enhanced interception using the charged surface of the activated carbon, in the presence of a colloid of a biologically active metal, is supplemented by the hydrophobic adsorption mechanism of the activated carbon. This hydrophobic mechanism is generally resistant to the impact of fouling by NOM, and is actually more effective under conditions of high ionic strength. Untreated portions of the carbon surface, with their oxygen-rich chemistry, tend to have a negative charge that can continue to adsorb positively charged particles. The combination of positive, negative, and hydrophobic surfaces presents a nearly insurmountable barrier for small particles to navigate. After treating the carbon with the microbiological interception enhancing agent, the presence of the biologically active metal and its associated counter ion on the active particles can be detected using X-ray fluorescence.

Method Of Making The Microbiological Interception Enhanced Filter Medium

The microbiological interception enhanced filter medium of the present invention can be made in accordance with processes known to one of skill in the art. Such processes include extrusion, molding, slip casting, immobilizing the active particles on a substrate, and the like. Exemplary processes are disclosed in U.S. Pat. Nos. 5,019,311, and 5,792,513.

The active particles are treated with the cationic material using means known to one of skill in the art such as, for example, spray coating. Preferably, the active particles are coated with about 0.5% to about 3% by weight, and more preferably about 1% by weight of the total weight of the microbiological interception enhanced filter medium. Once the cationic material is coated onto at least a portion of the active particles, the particles are exposed to the biologically active metal salt. A solution of the metal salt is infiltrated into the particles to cause precipitation of the biologically active metal on at least a portion of the surface of the active particles. The precipitation process accurately deposits the majority of the metal colloid directly adjacent to the cationic coating because the counter-ion associated with this coating reacts with the applied metal salt to form the colloidal particles. The metal salt can be sprayed onto the treated particles or otherwise applied using methods known to one of skill in the art. Solutions of the cationic material and the metal salt are preferably made with nearly ion-free water so that the counter-ions associated with the cationic material are drawn tightly against the cationic surface of the treated active particles and to eliminate unwanted ions that may cause uncontrolled precipitation of the biologically active metal into sites remote from the cationic surface.

Excess moisture is then removed from the particles, generally with heating or under vacuum, to a desired moisture content. Preferably, the moisture content should be less than about 10%, and more preferably less than about 5%, if the particles are to be subsequently extruded or molded using a thermoplastic binder.

Once the microbiological interception enhancing agent is coated on to at least a portion of the active particles, the active particles are ground to the desired size and potentially mixed with the binder material to form a homogenous mixture prior to immobilizing the active particles into a desired final form having the required microporous structure. The binder is chosen such that the melting point of the binder material is sufficiently lower than the melting point of the active particles so that the microbiological interception enhanced filter medium can be heated to activate the binder material, while the microporous structure does not melt and thereby lose porosity. The binder particles are preferably sufficiently evenly distributed throughout the active particles such that later, upon conversion to the microporous structure, the binder particles will entrap or bond to substantially all the active particles.

Binder materials useful in the present invention in coalescing the active particles into the microporous structure can potentially include any thermoplastic or thermoset material known in the art in either fiber, powder or particulate form. Useful binder materials can include materials such as, but not limited polyolefins, polyvinyl halides, polyvinyl esters, polyvinyl ethers, polyvinyl sulfates, polyvinyl phosphates, polyvinyl amines, polyamides, polyimides, polyoxidiazoles, polytriazols, polycarbodiimides, polysulfones, polycarbonates, polyethers, polyarylene oxides, polyesters, polyarylates, phenol-formaldehyde resins, melamine-formaldehyde resins, formaldehyde-ureas, ethyl-vinyl acetate copolymers, co-polymers and block interpolymers thereof, and combinations thereof. Variations of the above materials and other useful polymers include the substitution of groups such as hydroxyl, halogen, lower alkyl groups, lower alkoxy groups, monocyclic aryl groups, and the like.

A more detailed list of binders which can be useful in the present invention include end-capped polyacetals, such as poly(oxymethylene) or polyformaldehyde, poly(trichloroacetaldehyde), poly(n-valeraldehyde), poly(acetaldehyde), and poly(propionaldehyde); acrylic polymers, such as polyacrylamide, poly(acrylic acid), poly(methacrylic acid), poly(ethyl acrylate), and poly(methyl methacrylate); fluorocarbon polymers, such as poly(tetrafluoroethylene), perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), and poly(vinyl fluoride); polyamides, such as poly(6-aminocaproic acid) or poly(e-caprolactam), poly(hexamethylene adipamide), poly(hexamethylene sebacamide), and poly(11-aminoundecanoic acid); polyaramides, such as poly(imino-1,3-phenyleneiminoisophthaloyl) or poly(m-phenylene isophthalamide); parylenes, such as poly-2-xylylene, and poly(chloro-1-xylylene); polyaryl ethers, such as poly(oxy-2,6-dimethyl-1,4-phenylene) or poly(p-phenylene oxide); polyaryl sulfones, such as poly(oxy-1,4-phenylenesulfonyl-1,4-phenyleneoxy-1,4-phenyl-eneisopropylide ne-1,4-phenylene), and poly(sulfonyl-1,4-phenylene-oxy-1,4-phenylenesulfonyl4,4'-biphenylene); polycarbonates, such as poly-(bisphenol A) or poly(carbonyidioxy-1,4-phenyleneisopropylidene-1,4-phenylene); polyesters, such as poly(ethylene terephthalate), poly(tetramethylene terephthalate), and poly(cyclohexyl-ene-1,4-dimethylene terephthalate) or poly(oxymethylene-1,4-cyclohexylenemethyleneoxyterephthaloyl); polyaryl sulfides, such as poly(p-phenylene sulfide) or poly(thio-1, 4-phenylene); polyimides, such as poly(pyromellitimido-1, 4-phenylene); polyolefins, such as polyethylene, polypropylene, poly(1-butene), poly(2-butene), poly(1-pentene), poly(2-pentene), poly(3-methyl-1-pentene), and poly(4-methyl-1-pentene); vinyl polymers, such as poly(vinyl acetate), poly(vinylidene chloride), and poly(vinyl chloride); diene polymers, such as 1,2-poly-1,3-butadiene, 1,4-poly-1,3-butadiene, polyisoprene, and polychloroprene; polystyrenes; and copolymers of the foregoing, such as acrylonitrilebutadiene-styrene (ABS) copolymers. Polyolefins that can be useful include polyethylene, linear low density polyethylene, polypropylene, poly(1-butene), poly(2-butene), poly(1-pentene), poly(2-pentene), poly(3-methyl-1-pentene), poly(4-methyl-1-pentene), and the like.

Other potentially applicable materials include polymers such as polystyrenes and acrylonitrile-styrene copolymers, styrene-butadiene copolymers, and other non-crystalline or amorphous polymers and structures.

Preferred binder materials include polyethylene, poly(ethylene vinyl acetate), and nylons. Especially preferred as a binder is grade FN 510 microfine polyethylene commercially available from Equistar Chemicals, L.P., Tuscola, Ill., under the trade designation MICROTHENE® F.

The binder can have an average particle size of about 0.1 micron to about 250 microns, preferably about 1 micron to about 100 microns, and more preferably about 5 microns to about 20 microns. It is preferable that the binder material have a softening point that is significantly lower than a softening point of the active particles so that the microbiological interception enhanced filter medium can be heated to activate the binder material, while the microporous structure does not melt and thereby lose porosity.

The amount of binder material used is dependent upon how the microporous structure is formed whether by extrusion, molding, or other processes. For example, when the active particles are extruded or molded into a solid composite block, the binder material is preferably present in an amount of about 15% to about 22% by weight, and more preferably about 17% to about 19% by weight of the microbiological interception enhanced filter medium. When the active particles are immobilized on a substrate such as, for example, a nonwoven material, the binder material is preferably present in an amount of about 5% to about 20%, and preferably about 9% to about 15% by weight of the total composition.

One or more additives either in a particulate, fiber, whisker, or powder form may also be mixed with the active particles to aid in adsorption or absorption of other contaminants or participate in the formation of the microporous structure and interception of microbiological contaminants. Useful additives may include, but are not limited to, metallic particles, activated alumina, activated carbon, silica, polymeric powders and fibers, glass beads or fibers, cellulose fibers, ion-exchange resins, engineered resins, ceramics, zeolites, diatomaceous earth, activated bauxite, fuller's earth, calcium sulfate, other adsorbent or absorbent materials, or combinations thereof. The additives can also be chemically treated to impart microbiological interception capabilities depending upon the particular application. Such additives are preferably present in a sufficient amount such that the fluid flow in the resultant microbiological interception enhanced filter medium is not substantially impeded when used in filtration applications. The amount of additives is dependent upon the particular use of the filtration system.

Alternatively, the final microporous structure can be formed by slip casting or wet-forming the particles or fibers or such mixtures and subsequently causing binders or particles to sinter the ingredients together. In some cases, the particles can form their own binder as in bi-component fibers or low melting point resins. In some cases, the binder can be water soluble or cross-linkable resins or salts that when allowed to dry, or heated, or allowed to react, form the required bonds. Chemical binders can also be used as well as precipitated binders such as certain phosphate salts.

Filtration Systems Utilizing The Microbiological Interception Enhanced Filter Medium The microbiological interception enhanced filter medium of the present invention can be easily incorporated into prior art filtration systems that utilize particulate filtration medium immobilized as a solid composite blocks, flat, spiral or pleated sheets, monoliths, or candles. Preferably, a particulate prefilter is used in conjunction with the microbiological interception enhanced filter medium, positioned upstream from the microbiological interception enhanced filter medium, to remove as many particulate contaminants from the influent as possible prior to the influent contacting the microbiological interception enhanced filter medium.

EXAMPLES

The following examples are provided to illustrate the present invention and should not be construed as limiting the scope of the invention.

Porometry studies were performed with an Automated Capillary Flow Porometer available from Porous Materials, Inc., Ithaca, N.Y. Parameters determined, using standard procedures published by the equipment manufacturer, include mean flow pore size and gas (air) permeability. The flow of air was assayed at variable pressure on both the dry and wet microbiological interception enhanced filter medium.

Bacterial challenges of the microbiological interception enhanced filter media were performed using suspensions of *Escherichia coli* of the American Type Culture Collection (ATCC) No. 11775 to evaluate the response to a bacterial challenge. The response to viral challenges was evaluated using MS2 Bacteriophage ATTC No. 15597-Bi. Other microorganisms tested include *Brevundimonas diminuta* ATCC No. 4335, *Bacillus subtilis*, also known as BG, ATCC No. 9375. The Standard Operating Procedures of the ATCC were used for propagation of the bacterium and bacteriophage, and standard microbiological procedures, as well known in the art, were used for preparing and quantifying the microorganisms in both the influent and effluent of filters challenged with suspensions of the microorganisms.

Individual filters were tested in duplicate with each microorganism under a modified version of the NSF International Standard 53 cyst reduction test protocol. This protocol is designed to assess the performance of filters during an accelerated exposure to fine particulates to simulate accumulation of dirt. Filters were flushed with reverse osmosis/deionized (RO/DI) water and calibrated to an initial flow rate of 0.5 to 1.0 gallon/minute (gpm). The mean flow path of the filter media all were about 0.9 microns to 1.1 microns.

During testing, initial samples were drawn from both the influent and effluent sampling ports during the startup system flushing period to ensure that there was no background interference from an improperly disinfected test apparatus. The filter was then challenged with suspensions of the microorganisms, with samples being taken following a minimum 2L challenge solution, ensuring passage of the challenge water through the entire test stand prior to sampling.

All influent and effluent samples were serially diluted, as required, and plated in triplicate. In certain cases, carbon blocks of a given design were tested at several flow rates to ascertain their response to changing flow rate.

Activated carbon block filters having enhanced microbiological interception capability were prepared as follows. Twenty (20) pounds of 12×40 mesh acid-washed bituminous-coal-based activated carbon, obtained from Calgon Carbon Company, was gently mixed with a solution of 3% MERQUAT® 100 in de-ionized water to thoroughly coat the carbon particles and ensure that the MERQUAT® 100 had adsorbed onto at least a portion of the carbon particles. Thereafter, a solution of silver nitrate, 70 g crystalline silver nitrate in 1.0 L de-ionized water, was added to the MERQUAT® treated carbon to allow precipitation of the silver on at least a portion of the surface of the carbon particles in the form of silver chloride colloid. The treated carbon particles were dried at 135° C. until there was less than 5% moisture present in the carbon particles. Drying times varied between about 3 to about 5 hours. The dried carbon was ground in a double-roll grinder to 80×325 mesh size with approximately 14% by weight −325 mesh pan, and was mixed with FN510, a low density polyethylene binder material, at approximately 17% by weight. The mixture was extruded under suitable heat, pressure and temperature conditions, as described in U.S. Pat. No. 5,019,311. Resulting carbon block filters of various sizes were used to construct water filter systems by applying suitable end caps using a hot melt resin, as is well known in the art.

The filters were assayed for microbiological interception performance under initial clean conditions and then at intervals following dirt accumulation where the flow was reduced by 25%, 50% and 75% in comparison to the flow rate measured on the original, clean filter.

To achieve the required reduction in flow, "nominal" test dust challenge water was utilized. Nominal test dust is a silicate powder with particles roughly 0 to 5.0 microns in diameter and having 96% by weight of the particles in this range and 20% to 40% of the particles greater than 2.5 microns. When the required flow reduction has been accomplished, the nominal test dust challenge was curtailed and the filter flushed with 4.0 L of reverse osmosis/deionized (RO/DI) water to remove any residual test dust from the influent and effluent lines. The filter is then challenged with the suspensions of the microorganisms, as described above.

The efficacy of the microbiological interception enhanced filter medium of the present invention is shown in Tables I and II below.

TABLE I

LRVs Of Microbiological Interception Enhanced Activated Carbon Block Filter Medium

| Ex # | Filter Size O.D. × I.D. × Length (inches) | Flow Rate (gpm) | B. diminuta (LRV) | E. coli (LRV) | B. subtilis (LRV) | MS2 (LRV) |
|---|---|---|---|---|---|---|
| 1 | 1.85 × 0.375 × 2.94 | 0.50 | | | | 3.82 |
| 2 | 1.375 × 0.375 × 4.735 | 0.25 | 8.20 | | | 4.83 |
| 3 | 1.85 × 0.50 × 2.94 | 0.75 | | | | 2.15 |
| 4 | 2.00 × 0.75 × 2.55 | 0.75 | | | | 4.92 |
| 5 | 2.25 × 1.00 × 4.00 | 0.50 | 8.49 | 8.88 | 8.97 | 8.35 |
| 6 | 2.40 × 1.19 × 9.628 | 1.0 | | | | 5.79 |
| 7 | 1.50 × 0.375 × 6.055 | 0.50 | 8.80 | | | 5.31 |
| 8 | 1.50 × 0.375 × 6.055 | 0.60 | | | | 3.51 |
| 9 | 1.50 × 0.375 × 6.055 | 0.75 | | 8.79 | | 3.16 |
| 10 | 2.00 × 0.50 × 5.82 | 0.50 | 9.45 | 9.45 | 9.46 | 9.27 |

TABLE II

LRVs Of Microbiological Interception Enhanced Activated Carbon Block Filter Medium At Initial And Reduced Flow Rates

| Ex # | Initial Flow Rate (gpm) | Filter Size O.D. × I.D. × Length (inches) | Flow Reduction | E. coli (LRV) | MS2 (LRV) |
|---|---|---|---|---|---|
| 11 | 0.50 | 2.50 × 1.25 × 7.236 | 0% | 8.39 | 5.14 |
| | | | 25% | 8.46 | 5.73 |
| | | | 50% | 8.48 | 5.26 |
| | | | 75% | 8.61 | 6.99 |
| 12 | 0.50 | 1.50 × 0.375 × 6.055 | 0% | | 5.31 |
| | | | 25% | | |
| | | | 50% | | 7.03 |
| | | | 75% | | 8.17 |
| 13 | 0.60 | 1.50 × 0.375 × 6.055 | 0% | | 3.52 |
| | | | 25% | | 4.88 |

TABLE II-continued

LRVs Of Microbiological Interception Enhanced Activated Carbon Block Filter Medium At Initial And Reduced Flow Rates

| Ex # | Initial Flow Rate (gpm) | Filter Size O.D. × I.D. × Length (inches) | Flow Reduction | E. coli (LRV) | MS2 (LRV) |
|---|---|---|---|---|---|
|  |  |  | 50% |  | 4.89 |
|  |  |  | 75% |  | 5.71 |
| 14 | 0.75 | 1.50 × 0.375 × 6.055 | 0% | 8.79 | 3.16 |
|  |  |  | 25% | 8.79 | 4.27 |
|  |  |  | 50% | 8.76 | 4.08 |
|  |  |  | 75% | 8.74 | 4.86 |
| 15 | 0.50 | 2.25 × 1.00 × 4.00 | 0% | 8.88 | 8.35 |
|  |  |  | 25% | 8.88 | 9.50 |
|  |  |  | 50% | 8.87 | 8.34 |
|  |  |  | 75% | 8.91 | 8.22 |
| 16 | 0.50 | 2.00 × 0.50 × 5.82 | 0% | 9.45 | 9.27 |
|  |  |  | 25% | 9.41 | 9.25 |
|  |  |  | 50% | 9.48 | 9.25 |
|  |  |  | 75% | 9.44 | 9.25 |

The microbiological interception enhanced activated carbon block filter medium of the present invention provides greater than 8 log reduction of larger organisms such as *B. diminuta*, *E. coli* and *B. subtilis*. In fact, interception of these organisms was beyond the sensitivity of the test protocol in all cases. The results for MS2 penetration show no apparent correlation between wall thickness and levels of interception. This indicates that a traditional mechanical interception mechanism is not responsible for MS2 interception. However, there is a direct relationship between the log interception and the empty bed contact time (EBCT) of the filter. FIG. 1 shows a substantially linear relationship between the initial, clean filter log MS2 reduction and the EBCT of the filter indicating a diffusive interception mechanism with a requirement of approximately 6 seconds EBCT in order to achieve effective reduction of this bacteriophage in a microbiological interception enhanced filter medium having a mean flow path of about 0.9 to about 1.1 microns. For this reason, larger filters operating at lower flow rates perform more efficiently than small filters operating at elevated flow rates.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A filter medium comprising:
   a microporous structure comprising an array of active particles, said microporous structure having a mean flow path of less than about microns; and
   a microbiological interception enhancing agent comprising a cationic material having a medium to high charge density and a molecular weight greater than about 5000 Daltons, adsorbed on at least a portion of said microporous structure, and a biologically active metal in direct proximity to the cationic material and also on at least a portion of said microporous structure.

2. The filter medium of claim 1 wherein the active particles comprise of activated carbon, activated alumina, zeolites, diatomaceous earth, silicates, aluminosilicates, titanates, bone char, calcium hydroxyapatite, manganese oxides, iron oxides, magnesia, perlite, talc, polymeric particulates, clay, iodated resins, ion exchange resins, ceramics, or combinations thereof.

3. The filter medium of claim 1 wherein said microporous structure further includes a polymeric binder.

4. The filter medium of claim 1 wherein said microporous structure has a mean flow path of less than or equal to about 1 micron.

5. The filter medium of claim 1 wherein said microbiological interception enhancing agent consists of a cationic material on at least a portion of a surface of said microporous structure that has an associated counter ion therewith and wherein a biologically active metal is caused to precipitate with at least a portion of the counter ion associated with the cationic material.

6. The filter medium of claim 5 wherein the cationic material having a counter ion associated therewith is selected from the group consisting of amines, amides, quaternary ammonium salts, imides, benzalkonium compounds, biguanides, aminosilicon compounds, polymers thereof, and combinations thereof.

7. The filter medium of claim 1 wherein said microbiological interception enhancing agent comprises a cationic metal complex including a biologically active metal selected from the group consisting of silver, copper, zinc, cadmium, mercury, antimony, gold, aluminum, platinum, palladium, and combinations thereof.

8. The filter medium of claim 1 wherein the microbiologically enhanced interception agent is formed by treating at least a portion of said microporous structure with a cationic material comprising a homopolymer of diallyl dimethyl ammonium halide followed by precipitation of silver with at least a portion of the halide counter ion associated with the homopolymer of diallyl dimethyl ammonium halide.

9. The filter medium of claim 8 wherein the homopolymer of diallyl dimethyl ammonium chloride has a molecular weight of about 400,000 Daltons.

10. The filter medium of claim 1 wherein the cationic material is adsorbed, chemically bonded, or crosslinked to at least a portion of said microporous structure.

11. The filter medium of claim 1 wherein said microbiological interception enhancing agent has a charge density of greater than about 1 charge unit per about every 20 Angstroms of molecular length.

12. The filter medium of claim 1 wherein said microporous structure comprises a solid composite block of active particles.

13. The filter medium of claim 1 wherein said microporous structure comprises active particles immobilized into a flat sheet structure.

14. The filter medium of claim 1 wherein said microporous structure is formed by extrusion, molding, slip casting, powder coating, wet forming or dry forming of the active particles.

15. The filter medium of claim 1 wherein said filter medium provides greater than about 6 log reduction of microbiological contaminants in an influent when the influent has an empty bed contact time with said filter medium for less than about 12 seconds.

16. A filter system comprising:
   a housing having an inlet and an outlet;
   a filter medium situated within said housing in fluid communication with the inlet and outlet, said filter medium comprising:
      a microporous structure having a mean flow path of less than about 2 microns comprising active particles of activated carbon, activated alumina, zeolites, diatomaceous earth, silicates, aluminosilicates, titanates, bone char, calcium hydroxyapatite, manganese oxides, iron oxides, magnesia, perlite, talc, polymeric particulates, clay, iodated resins, ion exchange resins, ceramics, or combinations thereof; and a microbiological interception enhancing agent comprising a cationic material having a high charge density, a molecular weight greater than about 5000 Daltons and having an associated counter ion therewith, the cationic material adsorbed on at least a portion of the microporous structure, and wherein a biologically active metal is caused to precipitate with at least a portion of the counter ion associated with the cationic material, wherein a microbiologically contaminated influent flowing through said housing and contacting said filter medium has at least about 4 log reduction in microbiological contaminants in an effluent flowing from said housing.

17. The filter system of claim 16 wherein the active particles of the microporous structure are a solid composite block.

18. The filter system of claim 16 wherein the active particles of the microporous structure are immobilized into a flat sheet structure.

19. The filter system of claim 16 wherein the active particles of the microporous structure are slip cast, wet-formed or dry-formed.

20. A process of making a filter medium having enhanced microbiological interception capability comprising the steps of:

providing active particles having an average particle size of about 0.1 microns to about 5,000 microns;

treating the active particles with a microbiological interception enhancing agent comprising a cationic material having a high charge density and a molecular weight greater than about 5000 Daltons in combination with a biologically active metal; and forming the treated active particles into a microporous structure having a mean flow path of less than about 2 microns.

21. The process of claim 20 wherein the step of providing active particles comprises providing active particles of activated carbon, activated alumina, zeolites, diatomaceous earth, silicates, aluminosilicates, bone char, calcium hydroxyapatite, manganese oxides, magnesia, perlite, talc, polymeric particulates, clay, or combinations thereof.

22. The process of claim 20 wherein in the step of treating the active particles with a microbiological interception enhancing agent, the cationic material is selected from the group consisting of amines, amides, quaternary ammonium salts, imides, benzalkonium compounds, biguanides, aminosilicon compounds, polymers thereof, and combinations thereof.

23. The process of claim 20 wherein in the step of treating the active particles with a microbiological interception enhancing agent, the biologically active metal is selected from the group consisting of silver, copper, zinc, cadmium, mercury, antimony, gold, aluminum, platinum, palladium, and combinations thereof.

24. The process of claim 20 wherein the step of forming the treated active particles into a microporous structure further includes the addition of a binder.

25. The process of claim 24 wherein the step of forming the treated active particles into a microporous structure comprises compression molding.

26. The process of claim 24 wherein the step of forming the treated active particles into a microporous structure comprises extrusion.

27. The process of claim 20 wherein the step of forming the treated active particles into a microporous structure comprises immobilizing the treated active particles into a flat sheet substrate.

28. The process of claim 20 wherein the step of forming the treated active particles into a microporous structure comprises slip casting.

29. A process of making a filter medium having enhanced microbiological interception capability comprising the steps of:

providing active particles having an average particle size of about 0.1 microns to about 5,000 microns;

coalescing the active particles into a microporous structure having a mean flow path of less than about 2 microns; and treating the microporous structure with a microbiological interception enhancing agent comprising a cationic material having a high charge density and a molecular weight greater than about 5000 Daltons in combination with a biologically active metal.

30. The process of claim 29 wherein the step of providing active particles comprises providing active particles of activated carbon, activated alumina, zeolites, diatomaceous earth, silicates, aluminosilicates, bone char, calcium hydroxyapatite, manganese oxides, magnesia, perlite, talc, polymeric particulates, clay, or combinations thereof.

31. The process of claim 29 wherein the step of coalescing the active particles into a microporous structure further includes the addition of a binder.

32. The process of claim 29 wherein the step of treating the microporous structure with a microbiological interception enhancing agent comprises the steps of:

coating at least a portion of the microporous structure with a cationic material having a counter ion associated therewith; and causing precipitation of a biologically active metal with at least a portion of the counter ion associated with the cationic material on at least a portion of the microporous structure.

33. The process of claim 32 wherein in the step of coating at least a portion of the microporous structure with a cationic material having a counter ion associated therewith, the cationic material is selected from the group consisting of amines, quaternary ammonium salts, benzalkonium compounds, biguanides, aminosilicon compounds, polymers thereof, and combinations thereof.

34. The process of claim 32 wherein in the step of causing precipitation of a biologically active metal, the metal is selected from the group consisting of silver, copper, zinc, cadmium, mercury, antimony, gold, aluminum, platinum, palladium, and combinations thereof.

35. A method of removing microbiological contaminants from a fluid comprising the steps of:

providing a filter medium comprising
a microporous structure comprising active particles and having a mean flow path of less than about 2 microns; and
a microbiological interception enhancing agent comprising a cationic material having a medium to high charge density and a molecular weight greater than about 5000 Daltons in combination with a biologically active metal, adsorbed on at least a portion of said microporous structure;

contacting a microbiologically contaminated fluid to the filter medium for a period of time of less than or equal to about 12 seconds; and obtaining an effluent having greater than about 4 log reduction of microbiological contaminants.

36. The method of claim 35 wherein in the step of providing a filter medium, the microporous structure comprises active particles including activated carbon.

37. The method of claim 35 wherein in the step of providing a filter medium, the microbiological interception enhancing agent consists of a cationic material having a counter ion associated therewith, adsorbed on at least a portion of the microporous structure and wherein a biologically active metal is caused to precipitate with at least a portion of the counter ion associated with the cationic material.

38. The method of claim 35 wherein in the step of providing a filter medium, the microbiological interception enhancing agent consists of a metal-cationic material-halide complex wherein the cationic material is adsorbed, chemically bonded or crosslinked to at least a portion of said microporous structure.

* * * * *